United States Patent [19]

Mesina et al.

[11] 3,986,389

[45] Oct. 19, 1976

[54] GATING CONTROL SYSTEM IN ULTRASONIC INSPECTION APPARATUS

[75] Inventors: John Michael Mesina, Pittsburgh; Robert Anthony Sylvester, Coraopolis; Albert Lee Brautigam, Pittsburgh, all of Pa.

[73] Assignee: Jones & Laughlin Steel Corporation, Pittsburgh, Pa.

[22] Filed: Nov. 3, 1975

[21] Appl. No.: 628,575

[52] U.S. Cl. .............................. 73/67.9; 73/67.8 S
[51] Int. Cl.² ....................................... G01N 29/04
[58] Field of Search ........... 73/67.7, 67.8 R, 67.8 S, 73/67.9

[56] References Cited
UNITED STATES PATENTS

| | | | |
|---|---|---|---|
| 3,575,042 | 4/1971 | Lovelace | 73/67.8 S |
| 3,575,044 | 4/1971 | Gibbs | 73/67.9 |
| 3,640,122 | 2/1972 | Nusbickel | 73/67.9 |

Primary Examiner—Richard C. Queisser
Assistant Examiner—John P. Beauchamp
Attorney, Agent, or Firm—Buell, Blenko & Ziesenheim

[57] ABSTRACT

Apparatus for the ultrasonic pulse-echo inspection of moving metal strip having a defect signal gate and a backwall signal gate adjusted to provide a backwall signal gate interval of fixed width and a fixed delay between the closing of the defect signal gate and the opening of the backwall signal gate is provided with means for automatically varying the time of closing the defect signal gate in response to changes in the relative position in time of the backwall signal with respect to the backwall signal gate interval so as to keep that gate interval in coincidence with the backwall signal.

16 Claims, 7 Drawing Figures

GATING CONTROL SYSTEM IN ULTRASONIC INSPECTION APPARATUS

This invention relates to the ultrasonic pulse-echo inspection of metal workpieces. It is more particularly concerned with such apparatus for the inspection of traveling workpieces, such as metal sheet or strip, which tend to weave, or move back and forth laterally, as they travel.

In the ultrasonic pulse-echo inspection of metal articles the echo signals reflected from defects in the article must be separated from the echo signals reflected from the edge or from the opposite surface of the workpiece. This requirement creates no problems when the workpiece is stationary, either when the transducer is also stationary or is scanned over the work, as the movement of the transducer in the latter case is under control.

The situation is not the same with a traveling workpiece like metal sheet or strip. Because strip is never perfectly flat, it tends to weave or move laterally as it travels, in an irregular manner. Moreover, successive coils of strip are not necessarily of the same width. The result is that the position of the sheet edge signal with respect to a fixed index point is variable.

This is particularly troublesome in ultrasonic pulse-echo inspection of strip where the pulses are sent out transversely of the strip and are reflected by defects in the strip located between the transducer and the edge of the strip, and also by the edge itself. In such apparatus it is conventional to gate echo pulses electronically to the defect alarm circuits only in a desired inspection zone so as to exclude the edge or backwall pulse, as it is generally called. If the strip moves laterally, or if coils of different widths are inspected, it is necessary to re-adjust the gating apparatus. This, of course, can be done manually with the aid of the cathode ray tube display, but it is burdensome to the operator and invites error, particularly so when several transducers are used to achieve full width sheet inspection, and when rapid sheet weave is encountered. This difficulty has retarded the continuous ultrasonic inspection of metal strip, particularly steel strip.

It is an object of our invention to provide apparatus for automatically compensating for changes in location of the strip edge with respect to the transducer in ultransonic pulse-echo inspection of traveling metal strip. It is another object to provide such apparatus which is readily adapted to conventional ultrasonic pulse-echo inspection apparatus. Other objects of our invention will become apparent from the description thereof which follows.

An important feature of our invention is a double gate circuit for both defect and backwall signals, which is controlled by a tracking signal to adjust the position of both defect signal and backwall signal gate intervals with respect to the strip edge. When we speak of gate interval "position" we refer to its position on a cathode ray tube display, the horizontal sweep for which is controlled by the pulse generator, generally called the "pump". It is conventional to gate the defect signals as we have mentioned, the gate being closed for a time after each pump or transducer excitation pulse sufficient to exclude reverberation pulses from the surface of the strip and/or the transducer—strip interface, then being opened to receive defect signal echo pulses reflected from detects in the strip located between the transducer and a position just short of the strip edge, then closed to exclude the backwall echo pulse. It is also conventional to provide a second gate interval just wide enough to accommodate the backwall echo signal but spaced beyond the end of the defect signal gate interval. In our apparatus the initial closed time of the defect signal gate interval is fixed, the width of the backwall signal gate interval is fixed, as well as its spacing from the end of the defect signal gate interval, and the backwall signal gate interval is automatically made to coincide with the backwall signal by systematically controlling the time at which the defect signal gate interval end point occurs.

The systematic control of the end point of the defect signal gate interval is effected by electronic logic circuits which periodically search for and verify a backwall signal and which aperiodically repeat the verification of a verified backwall signal when certain criteria obtain.

The search operation for a true backwall signal varies systematically the width of the defect signal gate interval by an incrementally increasing amount so that the defect signal gate interval is widened during successive pump pulse periods from its predetermined minimum width toward a predetermined maximum width which exceeds the width of strip which can be inspected by the unit. When the backwall signal gate interval, which is moved out accordingly, coincides with a signal which may be a backwall signal, the defect signal gate interval width ceases to increase, but rather repeats at its value corresponding to the backwall signal gate interval coincidence in succeeding pump pulse periods until a search cycle is repeated. The verification logic comes into play immediately a putative backwall signal coincides with the backwall signal gate interval. If no backwall signal is found the search operation is repeated, upon the extension of the defect signal gate interval to its maximum width.

The verification feature of our invention comprises testing a signal received in the backwall signal gate interval to determine how well it repeats itself during a number of pump pulses. If the signal persists, that is, if it is determined to be the echo signal from the backwall and not some other response, the backwall gate is locked so that its width coincides with the backwall signal, and putative defects signals are then free to go to defect counting circuits, which are not part of our invention.

Means are provided to counteract backwall signal drift due to strip weave by periodically repeating search and verification operations and by aperiodically repeating verification upon command, determined by specific criteria. If verification fails at any time, the backwall signal search operation is reinitiated.

In the description of our invention which follows, signals which exceed a preset threshold voltage and which occur during the backwall signal gate interval are sometimes referred to as "backwall alarm signals". Such a signal is not necessarily a true backwall signal, although it may be proved to be so by subsequent verification. Likewise, signals which exceed a preset threshold voltage and which occur during the defect signal gate interval are sometimes called "defect alarm signals".

An embodiment of our apparatus presently preferred by us is illuatrated in the attached Figures to which reference is now made.

Figure 3:
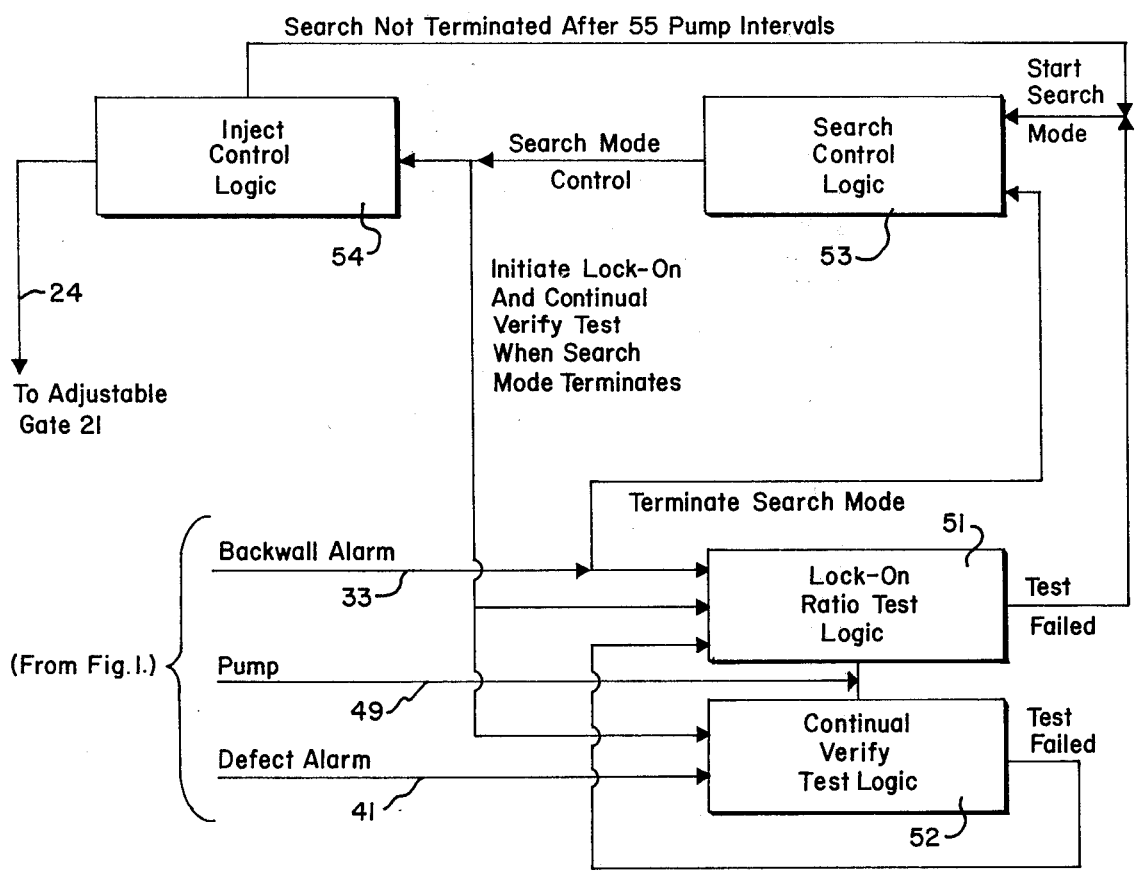
Figure 4:
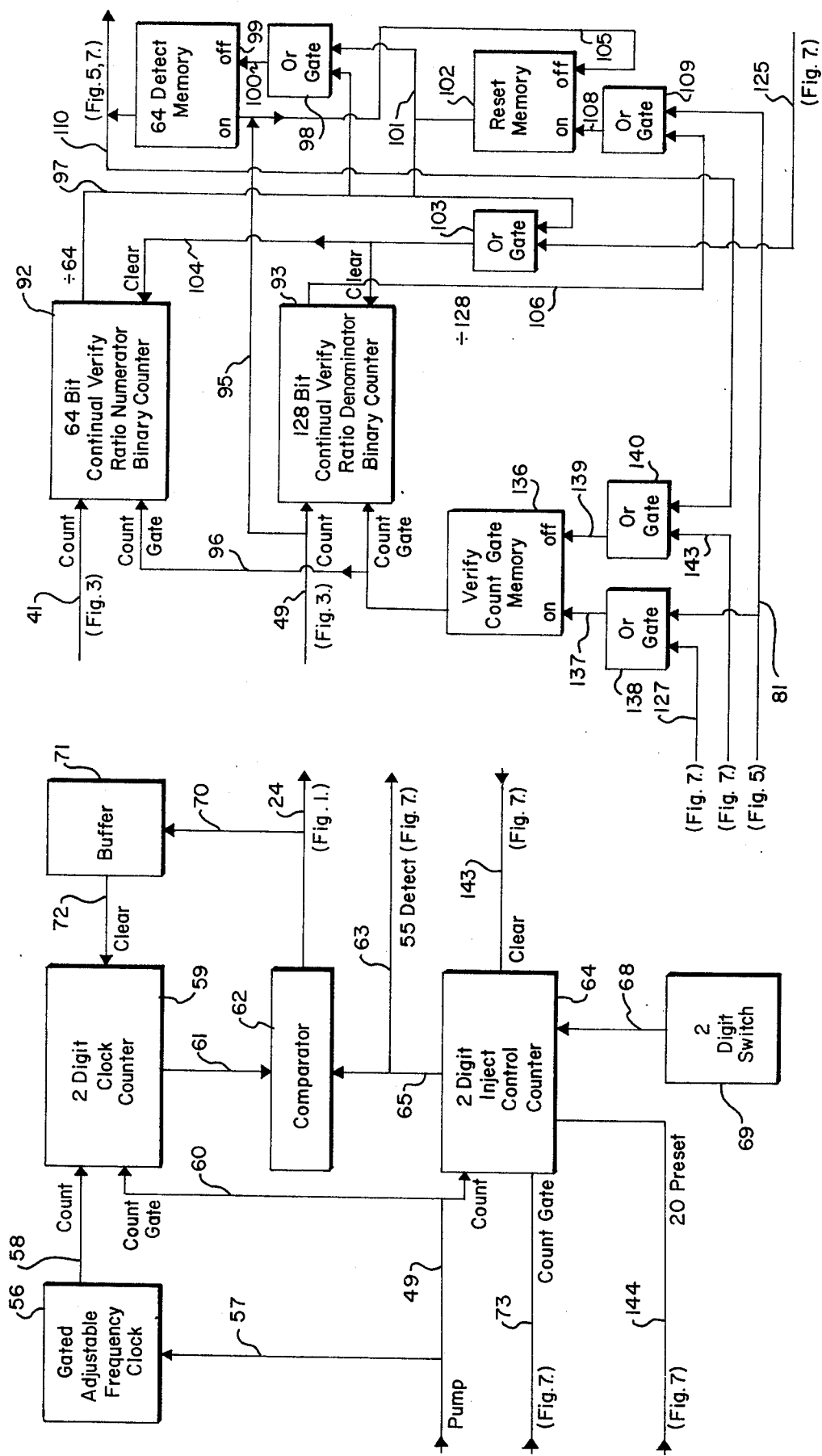
Figure 5:
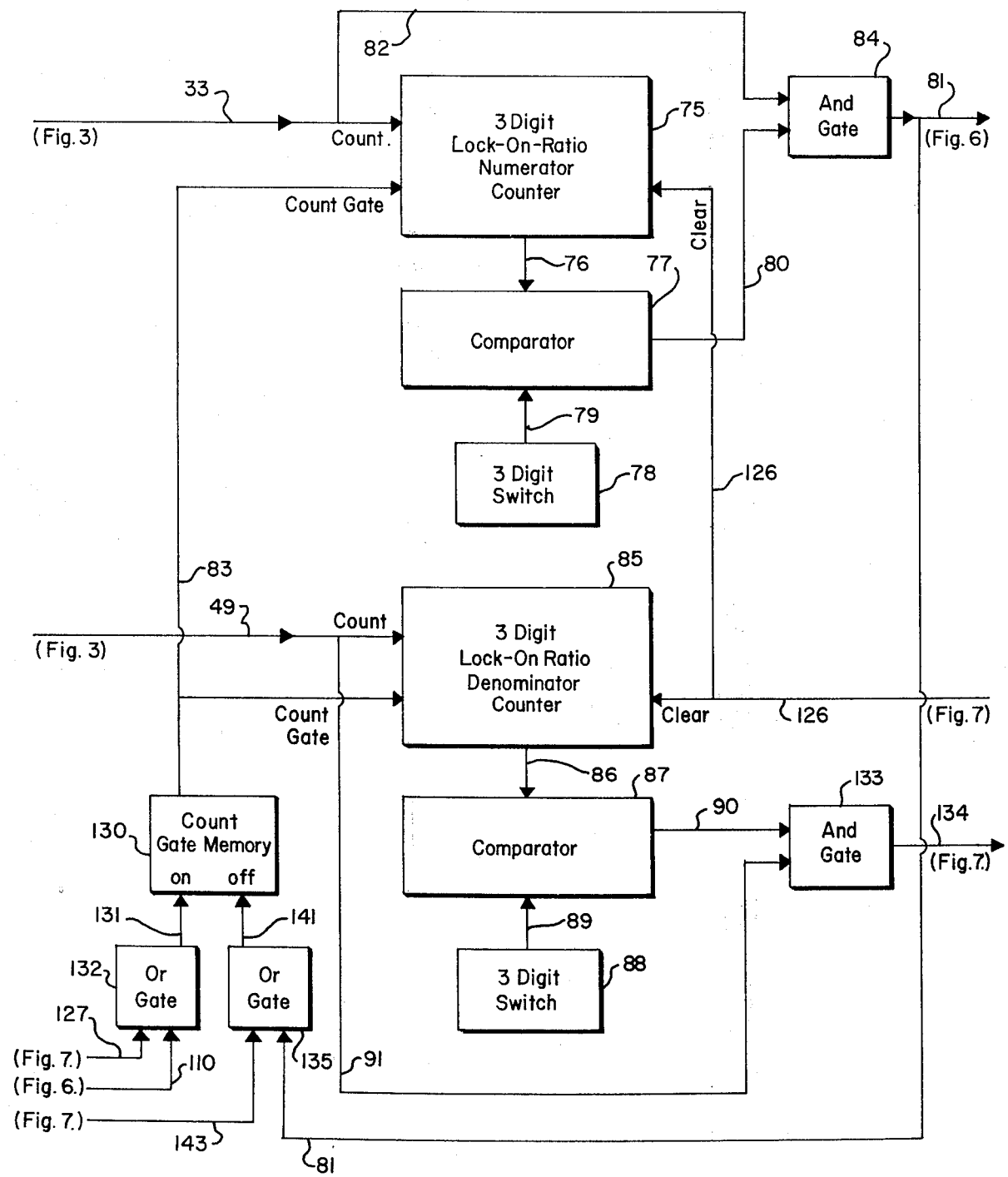
Figure 7:
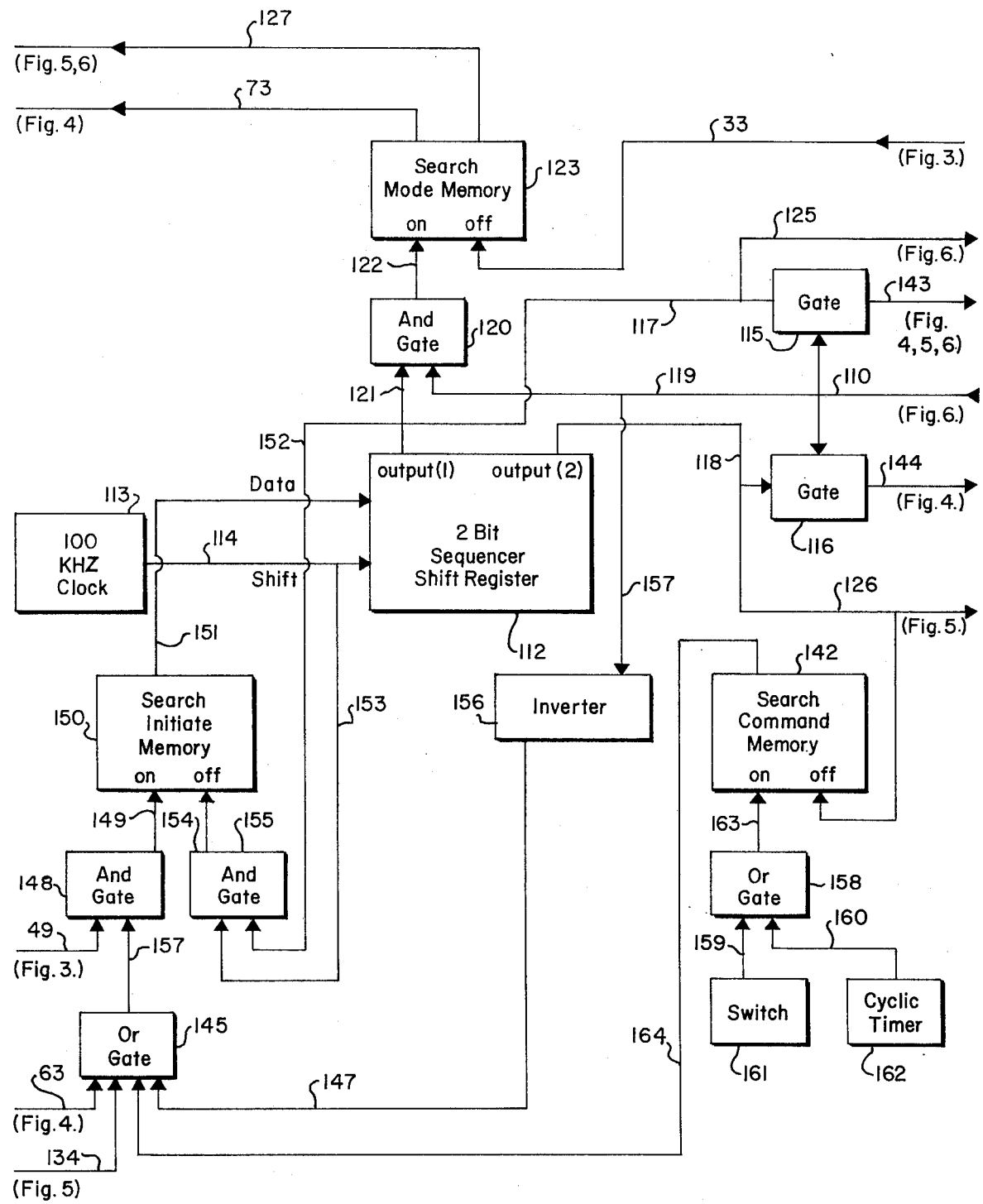

FIG. 3 is a generalized block diagram of the gate control logic, FIG. 4 is a block diagram of the inject control logic portion of the gate control logic of FIG. 3, FIG. 5 is a block diagram of the lock-on ratio test logic portion of the gate control logic, FIG. 6 is a block diagram of the continual verify test logic portion of the gate control logic, and FIG. 7 is a block diagram of the search control logic portion of the gate control logic.

Figure 1:
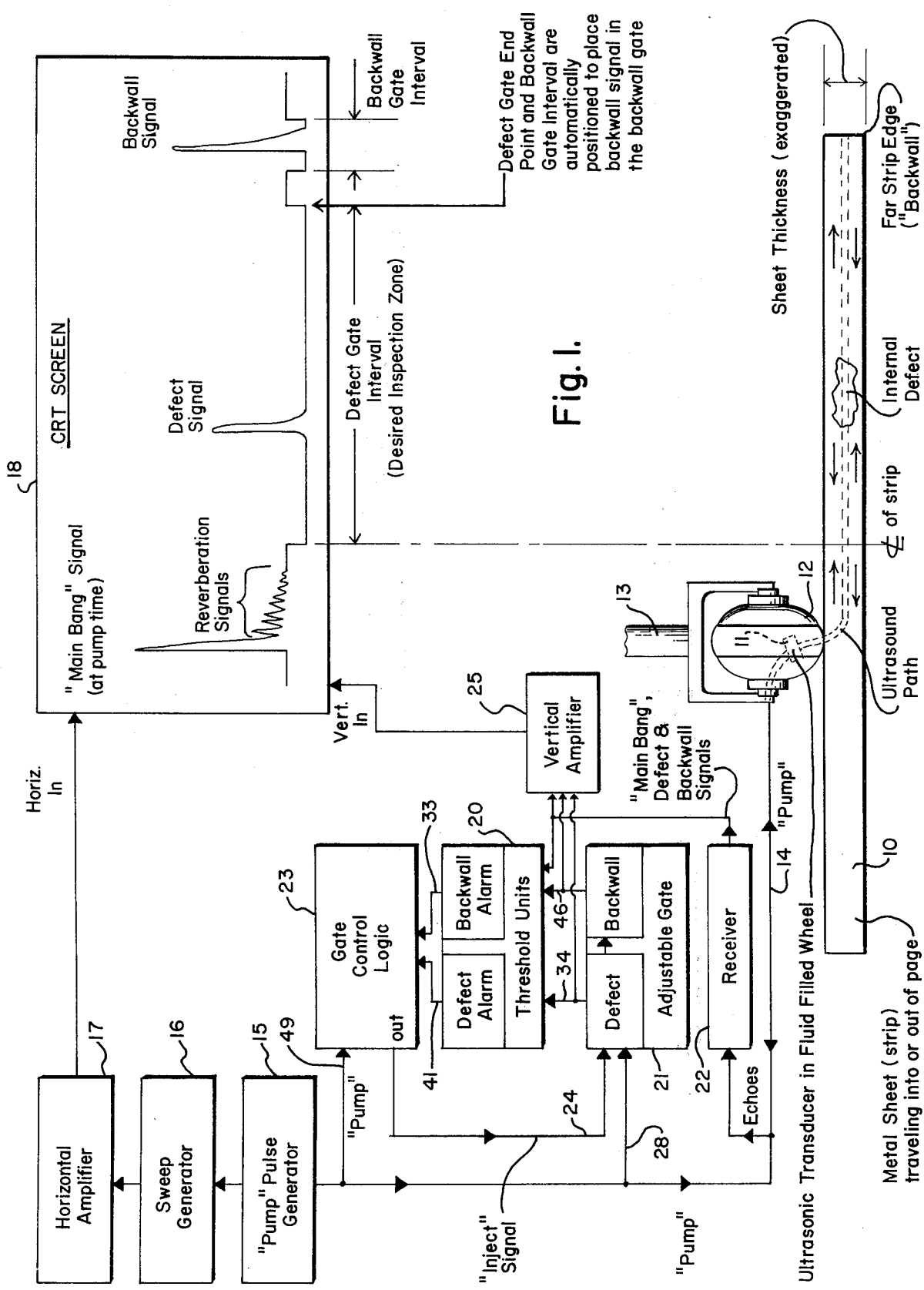
FIG. 1 is a partially representational and partially block diagram of our apparatus.

In FIG. 1 the strip 10 is shown in lateral cross section. As noted the strip is moving in a plane normal to the paper. An ultrasonic transducer 11 is mounted in a fluid-filled wheel 12 that is supported for free rotation about its axis in a mounting 13 which does not move with respect to strip 10. Wheel 12, however, rolls on the moving upper surface of strip 10. An electrical cable 14 connects transducer 11 through a wheel bearing with a pump, or pulse generator 15. The latter apparatus also supplies pump pulses to synchronize a sweep generator 16 which is connected through a horizontal amplifier 17 to the horizontal plates of a cathode ray display tube 18. All of the above elements are conventional.

Echo signals are received by transducer 11 and transmitted, also over cable 14, to a conventional receiver 22 from which they pass to conventional vertical amplifier 25 for display on cathode ray tube 18. The signals from receiver 22 are conducted to conventional defect signal and backwall signal threshold units 20. Those units pass on only signals having amplitudes greater than a preset value. Pump pulses are carried by cable 14 to the input 28 of adjustable gate 21, to be described hereinafter. Defect signal and backwall signal outputs 34 and 46, respectively, of adjustable gate 21 are conducted to the defect signal and backwall signal threshold units 20 and also to vertical amplifier 25 for display on cathode ray tube 18.

Echo signals which exceed threshold value and which occur during the defect signal gate interval are transmitted to the gate control logic 23 to be described hereinafter by conductor 41 and those which occur during the backwall signal gate interval are transmitted to logic 23 by conductor 33. Those signals, as has been mentioned, are more properly denominated defect alarm signals and backwall alarm signals, and are not necessarily true defect signals and true backwall signals.

Pulses from pump 15 are also transmitted to gate control logic 23 by conductor 49. That logic develops an inject signal which is transmitted to adjustable gate 21 over conductor 24, and thereafter controls the time at which the defect signal gate closes. Hence, it also controls the width of the defect signal gate interval, and the timing of the backwall signal gate interval.

Defect signals are taken off from the defect signal gate for analysis in conventional apparatus, not shown. Our invention is not concerned with the further treatment of defect signals, which may include counting, indicating and the like. Our apparatus does, however, distinguish between backwall alarm signals and defect alarm signals which may appear in the backwall signal gate interval, and between defect alarm signals and backwall alarm signals which may appear in the defect signal gate interval, as will be described.

ADJUSTABLE GATE 21

Figure 2:
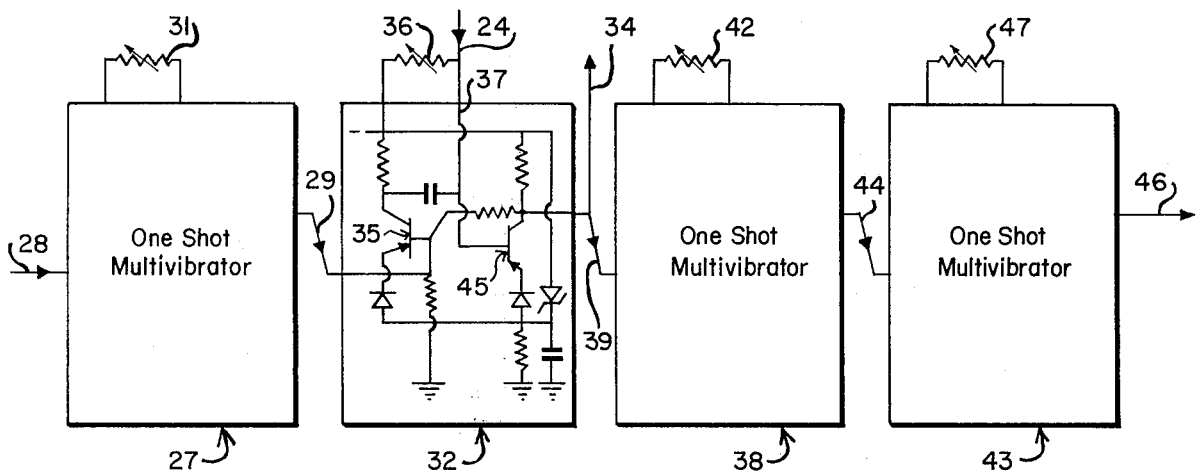
FIG. 2 is a block diagram of the adjustable gate component of our apparatus.

The circuitry of gate 21 is shown schematically in FIG. 2. It comprises four monostable or one-shot multivibrators 27, 32, 38 and 43 connected in tandem. Pump pulses over cable 14 are conducted to the input 28 of multivibrator 27. The output of multivibrator 27 is connected to the input of multivibrator 32 by lead 29. The output of multivibrator 32 is connected to the input of multivibrator 38 by lead 39. The output of multivibrator 38 is connected to the input of multivibrator 43 by lead 44. The output of multivibrator 32 is also connected by lead 34 to conventional gating means in threshold units 20 and the output of multivibrator 43 is likewise connected by lead 46 to separate conventional gating means in threshold units 20.

Multivibrators 27 and 32 comprise the defect signal gate and multivibrators 38 and 43 comprise the backwall signal gate. Conductors 34 and 46 are also connected to vertical amplifier 25. It is conventional to use a pair of one-shot multivibrators together with gating means to provide a gate interval in ultrasonic echo inspection apparatus and to take off signals which may be received during that gating interval.

The first and third multivibrators 27 and 28 are identical and are conducting in their quiescent condition. The second and fourth multivibrators 32 and 43 are likewise identical with one exception to be noted, and are non-conducting in their quiescent condition. The circuits of the multivibrators are conventional, that of multivibrator 32, for example, shown in detail in FIG. 2, comprising the usual regenerative cross-coupled input transistor 35 and output transistor 45. Multivibrators 27, 32, 38 and 43 are each provided with a variable element 31, 36, 42 and 47 respectively which adjusts the duration of the unstable portion of the cycle of each. Multivibrator 32 is provided with a trigger or second input 37, for a purpose to be described, which connects the base of output transistor 45 to lead 24, the inject signal conductor shown in FIG. 1.

Operation of gate 21 is initiated by a pulse from pulse generator 15. This pulse, often called the "pump", is applied simultaneously to sweep generator 16 and to transducer 11 to insure synchronization of the ultrasonic gating and the visual display mechanisms. The visual display on cathode ray tube 18 includes the "main bang" or transducer excitation signal, reverberation signals deriving from echoes at the interface of the wheel 12 and strip 10, the defect signal gate and the backwall signal gate intervals, and defect alarm and backwall alarm signals. Normally, only the defect signals are desired for inspection purposes, although the backwall signal attenuation is sometimes used as an indicator of dirty steel. The backwall or sheet edge signal, separated from other signals, is necessary to the operation of our apparatus. That signal occurs after every pump pulse, but a defect signal appears only when the ultrasonic pulse is reflected from a defect in the strip. The sequence to be described below is shown graphically on the cathode ray tube screen 18 of FIG. 1.

Multivibrator 27 is conducting in its quiescent condition. When the pump is applied to its input 28, multivibrator 27 is switched to the non-conducting state, and remains in that state for a period of time determined by the values of its coupling elements. This time is adjusted by variable element 31 to end after the reverberations from the strip surface have died out. Those reverberations thus are transmitted no further. Multivibrator 27 then switches back to its initial state, and this operation causes multivibrator 32 to switch from its quiescent non-conducting state to the conducting state. It remains conducting for a period of time which is adjusted by variable element 36. This time, however, can be shortened by applying a pulse to the base of transistor 45. The width of the defect gate interval is determined by the on or conducting time of multivibrator 32.

When multivibrator 32 switches off, multivibrator 38, which is conducting in its quiescent state, is switched off. The time during which this multivibrator remains off is adjusted by variable element 42 to provide a time separation between the end point of the defect signal gate interval and the starting point of the backwall signal gate interval. When multivibrator 38 switches back on, it triggers multivibrator 43, which is non-conducting in its quiescent state, to switch to the conducting state, and it stays on for a time adjusted by adjustable element 47 sufficient to form the backwall signal gate interval. The end point of the defect signal gate interval must be adjusted relative to the width of the strip being processed. Any change in the location of this end point causes the backwall gate interval to be displaced in the same direction by the same amount, without changing its width or its spacing from the defect signal gate interval. The automatic edge tracking of our invention is effected by varying the extent of the defect signal gate interval in the way above mentioned to insure that the sheet edge signal is positioned in the backwall signal gate interval. This variation is effected by our gate control logic, to be described.

GATE CONTROL LOGIC 23

The various elements of our gate control logic and their relations are shown in generalized block diagram in FIG. 3. The backwall alarm, defect alarm and pump signals are introduced into lock-on ratio test logic 51 and into continual verify test logic 52. If a backwall alarm signal occurs, it is introduced into search control logic 53 which signals inject control logic 54 to terminate its search for a backwall signal. Signals from inject control logic 54 to adjustable gate 21 over lead 24 are of a nature to fix the termination point of the defect signal gate interval for succeeding pulse echo intervals. If the signal fails to satisy lock-on ratio test logic 51 the latter sends a signal to search control logic 53 to initiate a search, and that logic so instructs inject control logic 54, which logic then causes our apparatus to search for a backwall signal in the way we have indicated and which will be more fully described hereinafter. Alarm signals in the defect signal gate interval are continually monitored by continual verify test logic 52 to ascertain if the backwall signal is drifting into the defect signal gate interval, and if it is, lock-on ratio test logic 51 is reactivated. The relations between the various elements of our gate control logic will be more easily understood from the description of those elements which follows.

INJECT CONTROL LOGIC 54

The circuitry of the inject control logic 54 is shown in FIG. 4. Its function is to generate pulses to trigger gate 21 during the searching operation. A gated adjustable frequency clock 56 of a frequency higher than that of pulse generator 15 is gated by pump pulses through conductors 49 and 57. The clock output is connected to the count input of a 2-digit clock counter 59 through conductor 58. The count gate of counter 59 is connected by conductor 60 to the pump through conductor 49. The output of counter 59 is connected to comparator 62 through conductor 61. The comparator 62 compares the output of counter 59 with the output 65 of a 2-digit inject-control counter 64. The comparator output supplies trigger pulses to gate 21 through conductor 24. These pulses also clear counter 59 after each pulse through conductor 70, buffer 71 and lead 72. The count input of counter 64 is also connected to conductor 60. Counter 64 may be preset to any number within its range through lead 144 (FIG. 7). In a test installation with which we are familar that number is 20, for reasons which will appear. The counter 64 may also be preset for calibration through lead 68 from 2-digit switch 69. Its output at a given number corresponding to the maximum width of strip which can be accommodated—55 in our test installation—is taken off over a conductor 63.

In operation of the above apparatus, the gated clock 56 is gated by pump pulses through lead 57 and the two-digit clock counter 59 is also gated by pulses from the pulse generator through lead 60. A gating pulse causes the clock 56 to start running and counter 59 to start counting from zero. The inject control counter 64 initially will contain some number equal to or greater than that preset through line 144, in the installation mentioned, 20. When the number in the clock counter 59 equals the number of inject control counter 64, the coincidence output of comparator 62 on line 24 will go out as a pulse to gate 21 and on line 70 will turn counter 59 off and reset it to zero. The next pump pulse will cause the inject control counter 64 to increment to the next higher count number, 21 in this case. The clock counter will then count from 0 to 21 and the comparator 62 will cause another pulse to go out over conductors 24 and 70. This sequence of operations will continue with clock counter 59 increasing by one number each time, causing the end point of the defect signal gate interval and the backwall signal gate interval to move out in increments across the cathode ray tube screen 18. If a backwall signal is found in the backwall signal gate interval, the inject control counter 64 will not be incremented on succeeding pump pulses but the gated adjustable frequency clock 56 and count gate of clock counter 59 will be enabled, permitting the clock counter 59 to count from zero to coincidence with the number contained in inject control counter 64, as previously described.

The frequency of gated clock 56 is adjusted so that each incremental pulse is equal to the time required for the ultrasound to travel out from and back to the transducer 11 through one inch of strip. Should the number of counts in the inject control counter 64 correspond to the maximum width of the strip which can be processed, 55 in our experimental installation, the cycle is caused to be repeated by the 55 detect signal on line 63 (FIG. 7).

The minimum count in inject control counter 64 is set at a value corresponding to a spacing somewhat less than the minimum anticipated distance between the transducer and sheet edge toward which the ultrasound is directed—i.e., the backwall. It is evident that transducer 11 cannot deal with echo signals coming from portions of the strip on each side of it, and, therefore, for full sheet width inspection, a second transducer is positioned some distance ahead or behind the first transducer 11 but offset the same amount on the other side of the center line of the strip. All the circuitry described herein is duplicated for the second transducer.

LOCK-ON RATIO TEST LOGIC 51

The circuitry for the lock-on ratio test logic is shown in FIG. 5. The purpose of this apparatus is to check for acceptably high repeatability of the alarm signal which terminates the search operation above described, and so confirm that the terminating signal is in fact the backwall signal. This is done by determining the ratio of alarm signal pulses in the backwall gate interval to pump pulses. A ratio of somewhat less than 1 but more than ½ is chosen as being indicative of sufficient repeatability of the signal to satisfy the lock-on condition. We find a ratio of 107 to 136 to be adequate. If 107 alarm signals are received before 136 pump pulses it indicates satisfactory lock-on. If, however, 136 pump pulses occur before 107 alarm signals the lock-on is considered defective and a new search is initiated.

A backwall alarm signal is transmitted over conductor 33 (FIG. 3) to the count input of 3-digit lock-on ratio numerator counter 75. The counter output is connected to comparator 77 by lead 76. The other input to comparator 77 is from a 3-digit switch 78 through lead 79. The coincidence output from comparator 77 on conductor 80 goes to one input of and gate 84. The other input is connected by lead 82 to the count input of numerator counter 75. The output of and gate 84 is connected by lead 81 to one input of or gate 135, the output of which is connected to the off input of count gate memory 130 through lead 141. The other input to or gate 135 is on reset lead 143 (FIG. 7). Pump pulses on lead 49 are fed to the counter input of 3 digit denominator counter 85. Its output is connected to comparator 87 by lead 86. A 3 digit switch 88 provides the other input to comparator 87 on lead 89. The comparator output on lead 90 is connected to one input of and gate 133. The other input of that gate is connected by lead 91 to the count input of denominator counter 85. The output of gate 133 is connected by lead 134 to gate 145 (FIG. 7). The on input of memory 130 is fed through conductor 131 by the output of or gate 132, the two inputs of which are lead 127 from the search mode memory (FIG. 7) and lead 110 from the 64 detect memory (FIG. 6). The on output of memory 130 is connected by conductor 83 to the count gates of both numerator and denominator counters 75 and 85.

As has been mentioned, the backwall alarm signal is applied to the count input of numerator counter 75 through line 33, and pump pulses are supplied on line 49 to the count input of denominator counter 85. Either a signal from lead 110 (FIG. 6) of continual verify test logic 52, to be described, or one on lead 127 (FIG. 7) from search control logic 53, to be described, turns on count gate memory 130 and enables the count gates of both counters 75 and 85, which then start counting the signal pulses and the pump pulses respectively. If numerator comparator 77 detects coincidence first, a lock-on ratio numerator detect signal will be generated on line 81, which signal turns off memory 130 and so disables the count gates of both counters 75 and 85. The numerator detect signal is also transmitted to the defect signal analyzing portion of the apparatus, not part of this invention, and gives it a go signal. If the denominator comparator 87 detects coincidence first, a denominator detect signal will be generated on line 134, which will initiate a new search through the search control logic 53 (FIG. 7) to be described. A reset pulse from that logic appearing on line 143 turns off count gate memory 130 and the numerator and denominator counters 75 and 85 are reset to zero by the sequencer (2) signal, also from that search control logic, on line 126.

CONTINUAL VERIFY TEST LOGIC 52

The circuitry of the continual verify test logic is shown in FIG. 6. This apparatus checks for drift of the backwall signal into the defect signal gate interval after lock-on is established. It does this by comparing the number of defect alarm signals in the defect signal gate interval with the number of pump pulses in a given period of time. A satisfactory ratio for this purpose is 64/128. If less than 64 defect alarm signals are received within 128 pump pulse intervals, the defect alarm signals are considered to be bona-fide. If 64 or more signals are received within 128 pump pulse intervals, drifting of the backwall signal into the defect signal gate interval is suspected to have occurred, and a lock-on ratio check, as has been described herein, is reinitated to test whether the backwall alarm signal is still in the backwall signal gate. While the lock-on ratio check is being conducted, the continual verify check is suspended. If the lock-on ratio check indicates that the suspected backwall signal drift into the defect signal gate interval has not occurred, the continual check is resumed. If the lock-on ratio check indicates that the lock-on is not valid, that is, a persistent alarm signal is not occurring, the suspected backwall drift into the defect signal gate is assumed to have, in fact, occurred, and a new search operation is initiated.

The principal elements of the continual verify logic are 64 bit continual verify ratio numerator binary counter 92 and 128 bit continual verify ratio denominator binary counter 93. The defect signal input is supplied to the count input of numerator counter 92 on lead 41. Pump pulses are applied to the count input of denominator counter 93 on lead 49. The count gates of both counters are tied together by lead 96 which is connected to the on output of verify count gate memory 136. The divided by 64 output of numerator counter 92 is connected by lead 97 to one input of or gate 98, the output of which is connected to the off input of 64 detect memory 99 by lead 100. The other input of or gate 98 is connected by lead 101 to the on output of reset memory 102. Lead 101 also connects to one input of or gate 103, the output of which is tied to the clear terminals of both counters 92 and 93 by lead 104. The other input of or gate 103 is connected by lead 125 to sequencer output 1 (FIG. 7).

The on input of 64 detect memory 99 is also connected to the pump through lead 95, and to the off input of reset memory 102 through lead 105. The divided by 128 output of denominator counter 93 is applied through lead 106 to one input of or gate 109, the output of which is connected by lead 108 to the on input of reset memory 102. The other input of or gate 109 is connected through lead 107 to one input of or gate 138. The on output of 64 detect memory 99 is applied through a conductor 110 to the counter gates of lock-on ratio numerator and denominator counters 75 and 85 previously described.

Conductor 110 is also connected to one input of or gate 140, the other input being connected to reset line 143 (FIG. 7). The output of or gate 140 is connected through lead 139 with the off input of memory 136. The output of or gate 138 is connected through lead 137 with the on input of memory 136. The output of or gate 138 is connected through lead 137 with the on input of memory 136. The outer input of or gate 138 is connected to conductor 127 (FIG. 7).

A signal from conductor 81 of FIG. 5 applied to conductor 96 via or gate 138 and verify count gate memory 136 actuates the gates of both numerator and denominator counters 92 and 93. Defect alarm signals on lead 41 will then be counted by numerator counter 92 and the pump signals on lead 49 will be counted by denominator counter 93. If the divide by 128 signal from counter 93 is generated before the divide by 64 signal from counter 92, reset memory 102 will be turned on until the next pump pulse turns it off. The on output of memory 102 resets both counters 92 and 93 to zero through or gate 103 and the clear inputs of those counters. Both counters then continue to count from zero as before. This cycle continues as long as the divide by 128 signal from counter 93 is generated before the divide by 64 signal from counter 92. If, however, the divide by 64 signal from that counter is generated before the divide by 128 signal, memory 99, which is normally on, will be turned off until the next pump pulse. The turning off of memory 99 will re-initiate the lock-on ratio check through lead 110 which, as has been mentioned, is connected to the count gates of lock-on ratio numerator and denominator counters 75 and 85 (FIG. 5). If the lock-on ratio check proves valid, the signal on lead 81 (FIG. 5) will be generated and re-initiate the continual verify check. If the lock-on is not valid, a new search operation will be initiated.

SEARCH CONTROL LOGIC 53

The search control logic 53 is shown in FIG. 7. It furnishes pre-set, reset and sequence signals to the apparatus previously described. Its principal component is 2 bit sequencer shift register 112.

Signals from a 100 KHZ clock 113, which frequency is higher than the frequency of the pulse generator, are supplied to the shift input of sequencer 112 over conductor 114. Output (1) of sequencer 112 is connected to the input of a gate 115 through lead 117 and output (2) of sequencer 112 is connected to the input of a gate 116 through lead 118. Those leads also furnish sequencer (1) and sequencer (2) signals to other logic elements previously described, over leads 125 and 126 respectively. The control inputs of both gates 115 and 116 are connected by lead 110 to the on output of 64 detect memory 99, shown in FIG. 6, and by lead 119 to one input of and gate 120. The other input of that gate is connected to sequencer output 1 by lead 121. The output of gate 120 is connected to the on input of search mode memory 123 through lead 122. The on output of that memory is connected through lead 73 to the count gate of inject control counter 64 (FIG. 4). The off input of memory 123 receives backwall alarm signals on lead 33. The off output of memory 123 is connected by lead 127 to one input of or gate 132 (FIG. 5) and one input of or gate 138 (FIG. 6).

Lead 118 from output (2) of sequencer 112 also connects to the off input of search command memory 142. The on input of that memory is connected through lead 163 to the output of or gate 158. The inputs of that gate are connected through leads 159 and 160 to an on/off switch 161 and to a cyclic timer 162, respectively. The on output of memory 142 is connected by conductor 164 to one input of a four-input or gate 145. Another input of gate 145 is connected through lead 147, inverter 156, and lead 157 to lead 119. The other two inputs are connected to the 55 detect signal line 63 (FIG. 4) and to lock-on ratio denominator detect line 134 (FIG. 5). The output of or gate 145 is connected by conductor 157 to one input of and gate 148. The other input of that gate receives pump signals on line 49. The output of and gate 148 is connected by lead 149 to the on input of search initiate memory 150, the on output of which is connected by lead 151 to the data input of sequencer 112. Output (1) of that sequencer is connected by lead 152 to one input of and gate 154. The other input of that gate is connected by lead 153 to line 114 from the 100 KHZ clock 113. The output of and gate 154 is connected by lead 155 to the off input of search initiate memory 150.

The search previously described can be initiated by any of four signals introduced into the four-input or gate 145, as follows:

1. A 55 detect signal over lead 63, that is, a signal from inject control logic 54 that the previous search has extended the full inspected width of the strip without locking on to a backwall signal.
2. A lock-on ratio denominator detect signal on lead 134, that is, a signal from lock-on ratio test logic 51 that the backwall alarm signal in the backwall signal gate interval does not appear with sufficient frequency to qualify as a backwall signal.
3. A signal from cyclic timer 162, at three second intervals in our installation, to provide periodic search operations to compensate for an undetectable drift of the backwall signal out of the backwall signal gate interval in a direction opposite to the defect signal gate interval.
4. A signal on line 164 from search command memory 142 initiated manually by closing switch 161, or periodically by the timing signals from cyclic timer 162. When the resulting signal on line 147 from or gate 145 coincides with a pump pulse on lead 49, it turns on search initiate memory 150, the on output of which is then connected to the data input of 2 bit sequencer shift register 112. The shift input of sequencer 112 receives the 100 KHZ clock impulses over lead 114.

In addition to the above inputs an inverted 64 detect signal on conductor 147 at the input to or gate 145 can initiate a pseudo-search with the intention only of resetting the lock-on ratio counters 75 and 85 for the reinitation of the operation during a backwall signal drift verification.

When search initiate memory 150 is turned on, its output is applied to the data input of sequencer 112, and during the next cycle of the 100 KHZ shift clock 113 the first stage and output (1) of sequencer 112 will be in the on state. The 64 detect memory 99 (FIG. 6) is normally on and so search mode memory 123 will also be turned on. During the following cycle of the shift clock 113, the on state of output (1) of sequencer 112 will permit search initiate memory 150 to be turned off, transferring the on state of output (1) to output (2). The on state of output (2) will turn search command memory 142 off. The next cycle of shift clock 113 will turn the second stage of sequencer 112 and output (2) off. Both stages of sequencer 112 will remain off until the next search operation turns the search initiate memory 150 back on.

Outputs (1) and (2) of sequencer 112 are the sources of sequencer 1 and sequencer 2 signals on leads 125 and 126 respectively, which go to control verify test logic 52 and lock-on ratio test logic 51 respectively. The outputs of sequencer gates 115 and 116 supply reset and preset pulses over leads 143 and 144, respectively, to input control logic 54, lock-on ratio test logic 51, and control verify test logic 52. Those gates are gated by the 64 detect signal on lead 110 from control verify test logic 52.

The search mode memory 123 remains in the on state until a backwall alarm signal appears at its off input. While search mode memory 123 is on, inject control counter 64 of inject control logic 54 (FIG. 4) is in the counting mode. When search mode memory 123 is turned off, inject control counter 64 stops counting and lock-on ratio count gate memory 130 (FIG. 5) and control verify count gate memory 136 (FIG. 6) are turned on by the on state of the off output of search mode memory 123.

As has been mentioned, 64 detect memory 99 (FIG. 6) is normally on. When a divide by 64 signal from numerator counter 92 is generated before a divide by 128 signal from denominator counter 93, 64 detect memory 99 is turned off. The termination of the signal from 64 detect memory 99 on line 119 (FIG. 7) is inverted into a positive pulse by inverter 156 and that pulse on line 147 turns on or gate 145, and gate 148, and search unit 150, so starting a pseudosearch cycle as previously described.

In our apparatus as described hereinabove, the various memory units are conveniently embodied in J-K master-slave and pulse triggered binary flip-flops. The on input of our memories is the set input and the off input the reset input of the flip-flop.

In our test installation the transducer 11 is positioned 10 inches from the center line of the strip. The signal is transmitted toward the far edge of the strip and the number 20 preset in input control counter 64 (FIG. 4) means that the beginning of the defect signal gate interval coincides with an echo signal received from a defect 10 inches from the center line of the strip on the opposite side from the transducer. The 55 detect signal generated by input control comparator 64 means that a backwall alarm signal from a strip edge more than 55 inches from the transducer 11, or 45 inches from the strip center line, cannot be received by the logic.

The term incrementally lagging trigger signals as used herein means a series of trigger signals each lagging a pulse from the signal generator by an interval which increases by a uniform amount from each pulse to the next pulse.

In the foregoing specification I have described presently preferred embodiments of my invention; however, it will be understood that my invention can be otherwise embodied within the scope of the following claims.

We claim:
1. In an ultrasonic inspection system for moving strip, the combination comprising means for generating a train of electrical pulses, transducer means connected with the pulse generator means adapted to be acoustically coupled to the strip and adapted to transmit ultrasonic pulses into the strip corresponding to the train of electrical pulses and to receive ultrasonic defect and backwall echo pulses from the strip and provide electrical signals corresponding thereto, defect signal gating means and backwall signal gating means connected with the transducer and adapted to receive electrical signals therefrom, the defect signal gating means comprising a trigger adapted to close the defect signal gate on receipt of a trigger signal, means connecting the output of the defect signal gating means to the input of the backwall signal gating means, those gating means being adjusted so that the closing of the defect signal gate causes the backwall signal gate to open after a time delay, and edge control means adapted to transmit a trigger signal to the trigger when a signal occupies the backwall signal gate interval, whereby varying the time of closing the defect signal gate varies the timing of the backwall signal gate but does not vary the time delay between the closing of the defect signal gate and the opening of the backwall signal gate.

2. Apparatus of claim 1 in which the defect signal gating means comprise a first two-transistor monostable multivibrator conducting in its quiescent state connected in tandem with a second two-transistor monostable multivibrator non-conducting in its quiescent state, the trigger being connected to the base of the output transistor of the second multivibrator.

3. Apparatus of claim 1 in which the backwall signal gating means comprise a first two-transistor monostable multivibrator conducting in its quiescent state, connected in tandem with a second two-transistor multivibrator non-conducting in its quiescent state, the first backwall monostable multivibrator being adapted to be switched off by the closing of the defect signal gating means.

4. Apparatus of claim 1 in which the edge control means includes search means adapted to transmit a succession of trigger signals to the trigger of the defect signal gate, one trigger signal following each pulse from the pulse generator, each trigger signal being timed a predetermined interval after its pulse greater than the interval between the previous trigger signal and its pulse, whereby the defect signal gate interval is incrementally increased in duration, and the search means are also adapted to terminate those trigger signals when a signal occurs in the backwall signal gate interval.

5. Apparatus of claim 4 in which the means adapted to transmit a series of trigger signals comprise a gated adjustable frequency clock of a frequency higher than that of the pulse generator, a clock counter driven by the clock, a pulse counter driven by pulses from the pulse generator, means for presetting the pulse counter to a predetermined number, comparator means for generating a trigger signal to the defect signal gate when the clock counter number coincides with the number in the pulse counter, means for clearing the clock counter by that trigger signal, means for gating the adjustable frequency clock and the clock counter by the pulses from the pulse generator, and means for increasing the number in the pulse counter by one corresponding to each pulse from the pulse generator.

6. Apparatus of claim 5 including means for adjusting the frequency of the gated adjustable frequency clock so that each count registered by the clock counter corresponds to the time required for a pulse to travel out from the transducer an integral unit of length and return to the transducer.

7. Apparatus of claim 5 including means for clearing the pulse counter and means for again presetting it to the predetermined number when the count in the pulse counter equals a second predetermined number greater than the first predetermined number and corresponding to the maximum width of strip which the system can inspect.

8. Apparatus of claim 7 including a fixed frequency clock of a frequency higher than that of the pulse generator, a 2 bit shift register, the shift input of which is connected to the fixed frequency clock, means for applying to the data input of the shift register the predetermined number signal generated by the pulse counter and in which the means for clearing the pulse counter are responsive to a signal from one output of the shift register gated by the pulses from the pulse generator, and the means for again presetting the pulse counter are responsive to a signal from the other output of the shift register also gated by pulses from the pulse counter.

9. Apparatus of claim 1 in which the edge control means includes means for distinguishing between a backwall signal and a defect signal in the backwall signal gate interval and means responsive to those first mentioned means to transmit incrementally lagging trigger signals to the defect signal gating means when those first mentioned means recognize the signal in the backwall signal gate interval to be a defect signal.

10. Apparatus of claim 9 in which the means for distinguishing between a backwall signal and a defect signal comprise means for counting the signal pulses in the backwall signal gate interval, means for comparing that count with a predetermined numerator count and for generating a numerator signal on coincidence thereof, means for counting the pulse generator pulses starting at the same time as the means for counting the signal pulses in the backwall signal gate interval, means for comparing the pulse generator pulse count wiith a predetermined denominator count larger than the numerator count and for generating a denominator signal on coincidence between the denominator count and the pulse generator pulse count, whereby when the numerator signal is generated before the denominator signal the signal in the backwall gate is recognized to be a backwall signal and when the denominator signal is generated before the numerator signal the signal in the backwall gate is recognized to be not a backwall signal.

11. Apparatus of claim 10 including means for closing the count gates of both counting means actuated by the numerator signal.

12. Apparatus of claim 10 including a fixed frequency clock of a frequency higher than that of the pulse generator, a 2 bit shift register, the shift input of which is connected to the fixed frequency clock, means for applying to the data input of the shift register the denominator signal, means for applying to the clear inputs of both counters a signal from one output of the 2 bit shift register, and means responsive to a signal from the other output of the 2 bit shift register, gated by pulses from the pulse generator, for interrupting the denominator signal to the data input of the shift register.

13. The apparatus of claim 10 in which the ratio of the predetermined numerator count to the predetermined denominator count is less than one but greater than one-half.

14. Apparatus of claim 1 in which the edge control means include means for monitoring the drift of the backwall signal into the defect gate interval comprising means for distinguishing between a backwall signal and a defect signal in the defect signal gate interval and means responsive to those distinguishing means to transmit incrementally lagging trigger signals to the defect signal gating means when those distinguishing means recognize the signal in the defect signal gate interval to be a backwall signal.

15. Apparatus of claim 14 in which the means for monitoring drift of the backwall signal into the defect signal gate interval comprise means for counting the signal pulses in the defect signal gate interval and generating a numerator signal when that count equals a first predetermined number, means for counting the pulse generator pulses starting at the same time as the means for counting the signal pulses in the defect signal gate interval and generating a denominator signal when that count equals a second predetermined number larger than the first predetermined number, and means for repeating the cycle actuated by the denominator signal when it is generated before the numerator signal.

16. Apparatus of claim 15 in which the counting means for defect signal pulses and the counting means for pulse generator pulses are binary counters and the second predetermined number is twice the first predetermined number.

* * * * *

UNITED STATES PATENT OFFICE
CERTIFICATE OF CORRECTION

PATENT NO. : 3,986,389
DATED : October 19, 1976
INVENTOR(S) : JOHN MICHAEL MESINA et al.

It is certified that error appears in the above-identified patent and that said Letters Patent are hereby corrected as shown below:

Column 1, line 67, "detects" should read --defects--.

Column 4, line 25, "28" should read --38--.

Column 9, lines 3, 4 and 5, beginning with "The output of or gate 138 is connected through lead 137 with the on inout of memory 136." should be deleted.

Column 9, line 5, "outer" should read --other--.

Signed and Sealed this

Twenty-sixth Day of April 1977

[SEAL]

Attest:

RUTH C. MASON
*Attesting Officer*

C. MARSHALL DANN
*Commissioner of Patents and Trademarks*